United States Patent
Kim et al.

(10) Patent No.: US 9,989,597 B2
(45) Date of Patent: Jun. 5, 2018

(54) CORRELATED DOUBLE SAMPLING FOR NOISE REDUCTION IN MAGNETORESISTIVE SENSORS AND SENSOR ARRAYS

(71) Applicant: The Board of Trustees of the Leland Stanford Junior University, Palo Alto, CA (US)

(72) Inventors: Kyunglok Kim, Belmont, CA (US); Drew A. Hall, La Jolla, CA (US); Shan X. Wang, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 85 days.

(21) Appl. No.: 14/832,949

(22) Filed: Aug. 21, 2015

(65) Prior Publication Data

US 2016/0054397 A1 Feb. 25, 2016

Related U.S. Application Data

(60) Provisional application No. 62/040,789, filed on Aug. 22, 2014.

(51) Int. Cl.
*G01N 27/00* (2006.01)
*G01N 15/06* (2006.01)
(Continued)

(52) U.S. Cl.
CPC ... *G01R 33/0029* (2013.01); *G01N 33/54326* (2013.01); *G01R 33/0041* (2013.01);
(Continued)

(58) Field of Classification Search
CPC ........ G01R 33/02; G01R 33/00; G01N 15/06; G01N 33/00; G01N 33/48; G01N 27/00
(Continued)

(56) References Cited

U.S. PATENT DOCUMENTS 3,781,574 A   12/1973   White et al.
6,803,555 B1  10/2004   Parrish et al.
(Continued)

OTHER PUBLICATIONS

Pannetier et al., "Noise in small magnetic systems—Applications to very sensitive magnetoresistive sensors", 2004, pp. 1-3, Journal of Magnetism and Magnetic Materials.
(Continued)

*Primary Examiner* — Brian J. Sines
(74) *Attorney, Agent, or Firm* — Lumen Patent Firm

(57) ABSTRACT

Correlated double sampling (CDS) for magnetoresistive (MR) sensors is provided. Here the MR sensor output is sampled at two closely spaced times. The first sample is MR signal+baseline+noise and is sampled when the modulated magnetic field is non-zero. The second sample is baseline+noise only because it is sampled when the modulated magnetic field is zero. The difference between the first and second samples will have significantly reduced low frequency noise and baseline cancellation. Modulation of the electrical bias provided to the MR sensor can be used to provide a baseline signal for temperature compensation. In a second aspect, we provide MR sensor arrays having input and output multiplexing and demultiplexing for row and column line selection, in combination with a per-sensor switch to prevent noise accumulation and bandwidth reduction from idle MR sensors.

13 Claims, 16 Drawing Sheets

(51) Int. Cl.
*G01R 33/02* (2006.01)
*G01R 33/00* (2006.01)
*G01R 33/12* (2006.01)
*G01V 3/08* (2006.01)
*G01V 3/38* (2006.01)
*G01N 33/543* (2006.01)

(52) U.S. Cl.
CPC .......... *G01R 33/1269* (2013.01); *G01V 3/08* (2013.01); *G01V 3/38* (2013.01)

(58) Field of Classification Search
USPC ........... 422/68.1, 82.01, 82.02; 436/43, 149, 436/150, 151
See application file for complete search history.

(56) References Cited

U.S. PATENT DOCUMENTS

| | | | |
|---|---|---|---|
| 9,612,262 B1* | 4/2017 | Nehmeh | G01R 15/202 |
| 2002/0115925 A1* | 8/2002 | Avrin | A61B 5/04005 |
| | | | 600/407 |
| 2005/0171421 A1* | 8/2005 | Eden | G01R 33/032 |
| | | | 600/409 |
| 2011/0169488 A1 | 7/2011 | Mather | |
| 2013/0116955 A1* | 5/2013 | Williams | G01R 15/20 |
| | | | 702/64 |
| 2013/0221949 A1* | 8/2013 | Liu | G01R 33/0011 |
| | | | 324/202 |
| 2013/0300402 A1* | 11/2013 | Liu | G01R 33/09 |
| | | | 324/202 |
| 2014/0300348 A1* | 10/2014 | Deak | G01R 33/0035 |
| | | | 324/202 |
| 2014/0323337 A1 | 10/2014 | Cardoso et al. | |
| 2015/0253412 A1* | 9/2015 | Jost | G01R 33/09 |
| | | | 324/202 |
| 2015/0331065 A1* | 11/2015 | Engel | G01R 33/0029 |
| | | | 324/252 |

OTHER PUBLICATIONS

Wang et al., "An ultrasensitive CMOS magnetic biosensor array with correlated double counting noise suppression", 2010, pp. 616-619, IEEE Microwave Symposium Digest.

Liu et al., "Magnetic relaxation detector for microbead labels", 2012, pp. 1056-1064, IEEE J. Solid-State Circuits.

Xu et al., "A highly sensitive CMOS digital Hall sensor for low magnetic field applications", 2012, pp. 2162-2174, Sensors.

Hall et al., "A 256 pixel magnetoresistive biosensor microarray in 0.18 um CMOS", 2013, pp. 1290-1301, IEEE J. Solid-State Circuits.

* cited by examiner

CORRELATED DOUBLE SAMPLING FOR NOISE REDUCTION IN MAGNETORESISTIVE SENSORS AND SENSOR ARRAYS

CROSS REFERENCE TO RELATED APPLICATIONS

This application claims the benefit of U.S. provisional patent application 62/040,789, filed on Aug. 22, 2014, and hereby incorporated by reference in its entirety.

FIELD OF THE INVENTION

This invention relates to magnetoresistive (MR) sensors.

BACKGROUND

Magnetoresistance is a change in electrical resistance that depends on magnetic field. The presence of an object of interest (e.g., a magnetic particle) can be sensed by the change in resistance of the MR sensor. Biological assays can be constructed by making magnetic particles bind to MR sensors under biologically specific circumstances. For example, if the MR sensors and magnetic particles are coated with an antigen and a corresponding antibody, respectively or vice versa, then binding of antibody to antigen can be detected via the MR effect.

In biological applications, it is often desired to employ a large array of MR sensors in order to conduct large-scale assays. In such cases, system performance is often limited by electrical noise, and noise mitigation is also of more general interest for all applications of MR sensors. Accordingly, it would be an advance in the art to mitigate noise in MR sensors, especially in connection with arrays of MR sensors.

SUMMARY

The present work has two aspects, which can be practiced individually or in combination. The first aspect relates to use of correlated double sampling (CDS) for MR sensors combined with modulation of an applied magnetic field. The second aspect relates to MR sensor arrays having input and output multiplexing and demultiplexing for row and column line selection, in combination with a per-sensor switch to prevent noise accumulation from idle MR sensors.

This work provides correlated double sampling in connection with MR sensors. The MR sensor output is sampled at two closely spaced times. The first sample is MR signal+ baseline+noise, and the second sample is baseline+noise only. The difference between the first and second signals will have baseline cancellation and significant noise suppression because of the relatively low noise frequencies involved and because both signals are provided by the same circuitry. Further elaborations of this approach (e.g., as described below) can be used to provide low-noise temperature correction for MR sensors, and suitable architectures for low-noise MR sensor arrays.

More specifically an MR sensor array can include an analog multiplexer (Mux) and demultiplexer (deMux) to provide column line and row line selectors (or vice versa). Introduction of the Mux and the deMux dramatically reduces the number of input/output pads of the microarray chip, which in turn greatly simplifies the interface with sensor readout circuits. Adopting a two dimensional matrix structure allows sensor elements to be individually accessible in time and also improves power efficiency of the array.

Each magnetoresistive sensor in an array can have its own on/off switch. Using such switches, only sensors in selected pixels are accessible at the readout time, while the other sensors are disconnected from the row and/or column lines. This advantageously prevents noise from unselected sensors from being transmitted to the input of readout circuits. Another advantage of this methodology is to preserve the signal bandwidth of the readout channel by disconnecting unread sensors from the channel. Without it, the signal bandwidth is narrowed due to the unread sensors connected to the channel. The switches can be metal-oxide-semiconductor devices or other semiconductor devices such as switching diodes. The number of switching devices per sensor element can be one or more.

This can provide a broader scalability of magnetoresistive sensor arrays which can accommodate more than 1,000 sensors per array. In medical applications, demand for large-scale sensor arrays accommodating numerous types of analytes such as human proteins is increasing. This work provides architectures for large-scale magnetoresistive sensors array without disadvantages in channel bandwidth and noise performance. Correlated double sampling and temperature correction techniques can be used to build temperature insensitive and high throughput data acquisition systems using magnetoresistive sensors, although the techniques are suitable for arrays with less than 1000 sensors as well.

These approaches are broadly applicable, e.g., in both biological and non-biological settings. Applications include medical, mobile and industrial applications of magnetoresistive sensors. Exemplary medical applications include diagnosis and/or prognosis of a disease and drug discovery targeting a specific disease. For mobile and industrial applications, quantification of a minute change of the magnetic field and/or magnetically actuated reaction can be provided.

Significant advantages are provided.

1. Correlated double sampling and temperature correction methods can provide ultra-high throughput in data acquisition in a large-scale sensor array with large dynamic range and high precision. For example, the readout speed per channel can be 100× faster with the CDS approach than with prior approaches (e.g., lock-in double modulation techniques as described below).

2. The MR sensor array architectures can provide constant channel bandwidth and fixed noise performance regardless of the number of sensors in the array.

Several variations are possible. The biasing of the magnetoresistive sensors can be provided by a bias voltage or by a bias current. A modulated magnetic field of square, sinusoidal or return-to-zero waveform are suitable for CDS techniques. More generally, any modulation waveform which includes a zero magnetic field portion of the waveform can also be utilized.

DETAILED DESCRIPTION

A) Introduction

Molecular diagnostics is used extensively today by the medical community for disease diagnosis, prognosis, therapy monitoring and drug discovery. As researchers begin to understand the numerous biomarkers associated with complex diseases such as cancers, new sensing technologies emerge to effectively detect and measure the biomarkers of interest in patients' samples. The demand for high sensitivity, broad linear dynamic range, and large multiplexing capability requires high performance sensing technologies. Conventional optical techniques, which rely on a fluorescent tag to label biomarkers of interest, have a limited dynamic range due to the optical background noise and also inherently have relatively low sensitivity. By replacing the fluorescent tag with a magnetic nanoparticle and the bulky optics with a magnetoresistive (MR) sensor, researchers have achieved highly sensitive detection with a broad linear dynamic range.

Figure 1A:
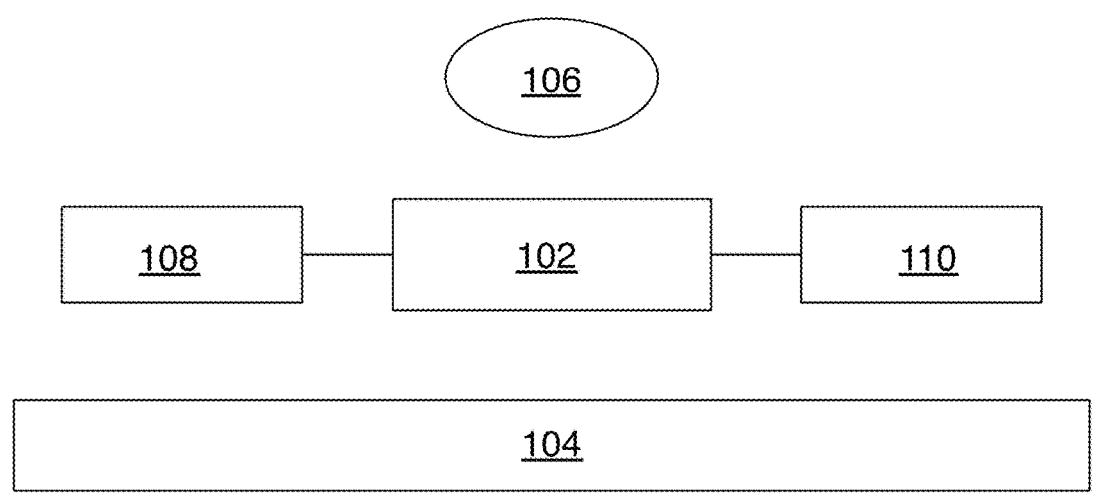
FIG. 1A is a block diagram of an embodiment of the invention.
Figure 1B:
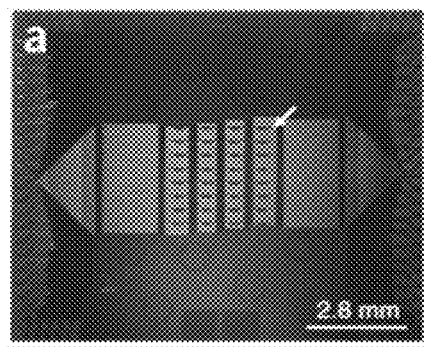
FIGS. 1B-D are exemplary images of magnetoresistive sensors.
Figure 1C:
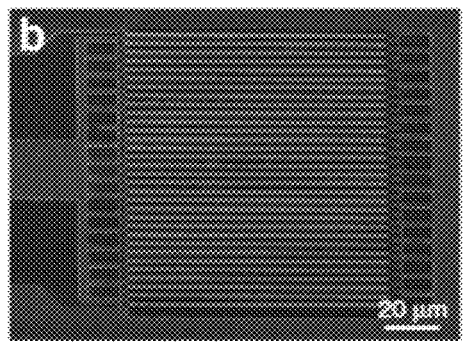
Figure 1D:
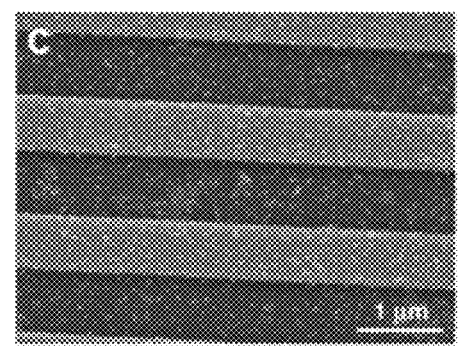

FIG. 1A schematically shows a magnetic particle 106 in proximity to a MR sensor 102. The presence of the magnetic field from magnetic particle 106 at MR sensor 102 changes the electrical resistance of MR sensor 102. FIGS. 1B-D show images of exemplary MR sensors. FIG. 1B is an image of a 64 element giant magnetoresistive (GMR) spin valve sensor array. FIG. 1C is a magnified view of a single sensor in the array of FIG. 1B. Multiple GMR sensor strips form the GMR sensor. FIG. 1D is an image showing super paramagnetic nanoparticles on the surface of the GMR sensor.

The MR biosensor typically includes elaborately engineered thin film stacks of magnetic and non-magnetic materials. Multiple narrow and long strips of the thin film stacks form a MR sensor (FIGS. 1B-C). It senses the minute change of the induced magnetic field by the number of magnetic nanoparticles adjacent to it in the circumstance of the external magnetic field (FIG. 1D). The number of magnetic nanoparticles is proportional to the degree of the reaction between the antibodies on the sensor surface and the analytes. If the antibodies are paired with the target analytes, the resistance of the MR sensor changes.

Figure 2A:
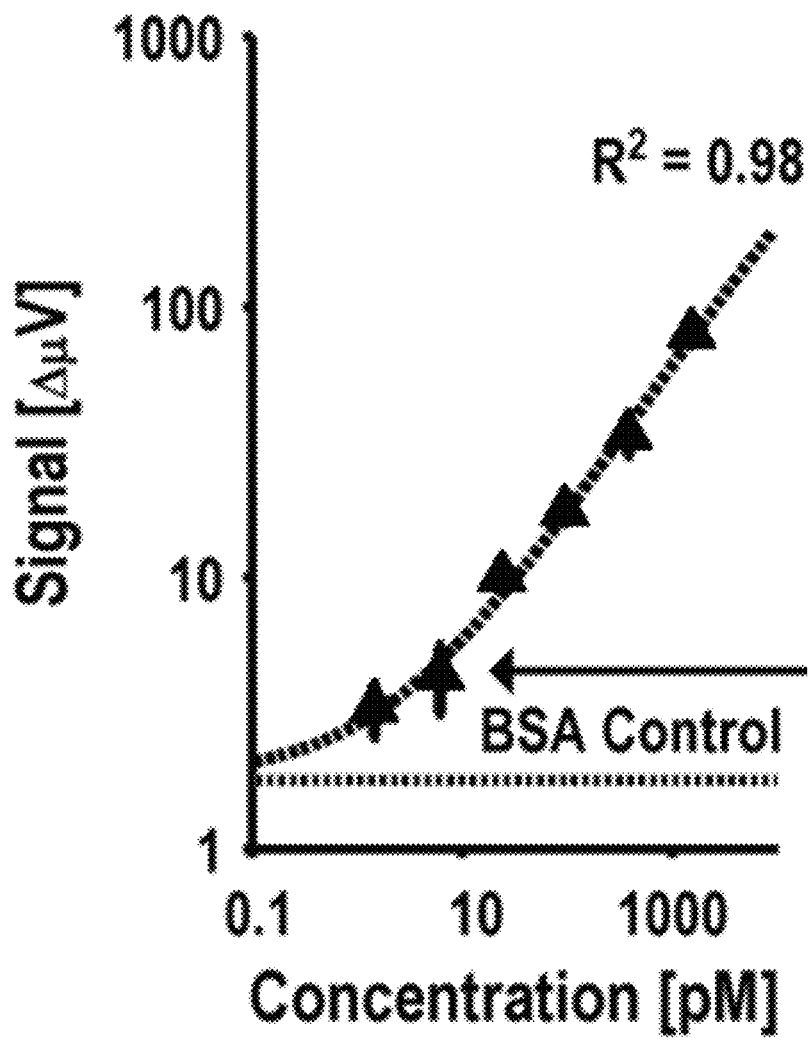
FIG. 2A shows an exemplary binding curve for biomarker detection.
Figure 2B:
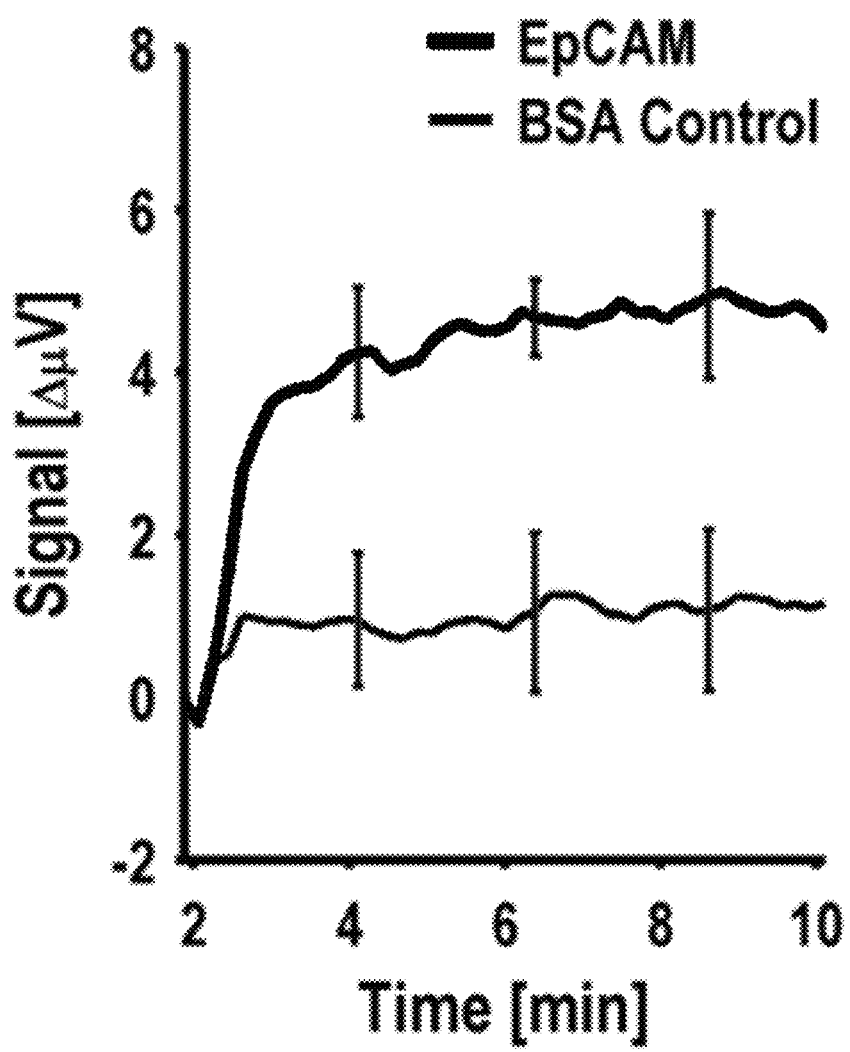
FIG. 2B shows exemplary transient binding curves for biomarker detection.

FIGS. 2A-B show examples of specific biomarker detection by magneto-resistive sensors. FIG. 2A is a standard binding curve (Signal vs. concentration of CEA (Carcinoembryonic antigen, which is a cancer biomarker)). FIG. 2B shows transient binding curves (Signal vs. time) of three biomarkers. BSA and epoxy is a biological control and a reference, respectively. A minute signal of interest is distinguishable from the control.

Figure 3A:
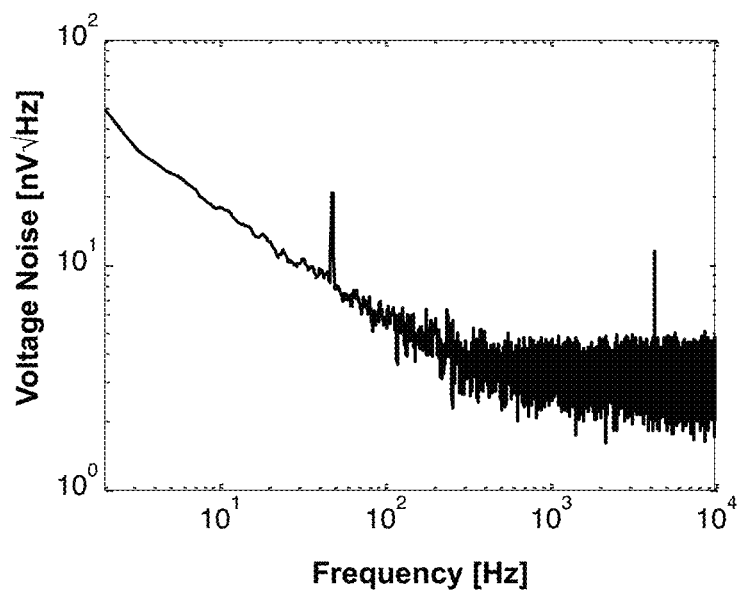
FIGS. 3A-B show exemplary noise spectra for MR sensors and electronics.

Since the MR sensor has both magnetic and resistive characteristics, it generates noises such as 1/f noise, thermal noise, Barkhausen noise and so on. Barkhausen noise can be eliminated by utilizing shape anisotropy of the film strips and/or applying strong magnetic field to the sensor at the preconditioning step. If Barkhausen noise is excluded, 1/f noise dominates the total noise from the sensor at the low frequency range and thermal noise at the frequency range over the corner frequency of 1/f noise. FIG. 3A shows voltage noise measured from an exemplary MR sensor at fixed current. Input voltage noise of the sensor is 4.76 $nV_{rms}/\sqrt{Hz}$, which is close to the theoretical thermal noise floor $4k_BTR$. The 1/f noise corner frequency is at 285 Hz.

Figure 3B:
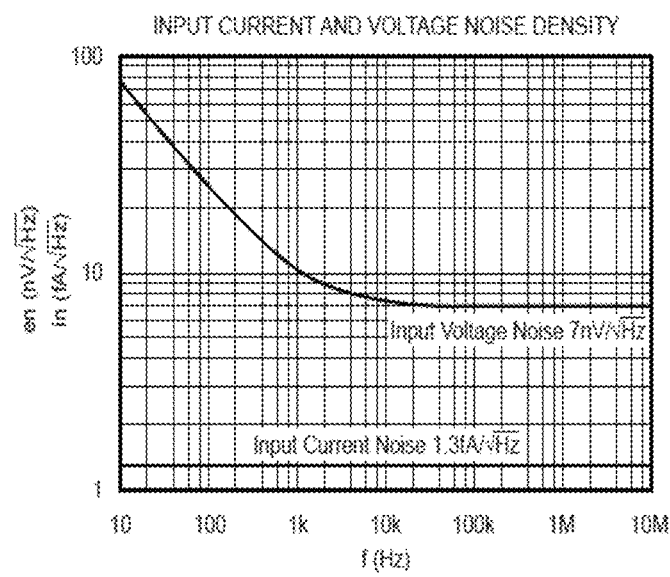

The signal of interest is commonly located at low frequency range, so 1/f noise degrades the limit of signal detection. Not only 1/f noise from the sensor, but 1/f noise caused by data acquiring electronics is also problematic. FIG. 3B shows an example of the noise profile of a commercial operational amplifier (OPA656 from Texas Instruments, Inc.), which shows the dominant 1/f noise at lower frequency range. 1/f noise is noise that has a power spectral density proportional to 1/f. The corner is where the 1/f noise intersects the thermal noise.

In order to avoid the degradation of signal-to-noise ratio by 1/f noise of the data acquisition electronics, the frequency division multiplexing (FDM) has been used to measure the change of MR ratio of the sensors for the biological reactions between analytes and antibodies. However, as the size of the sensor array increases, the non-ideal phenomena in FDM such as harmonic distortion become more prominent. Furthermore, the data acquisition time for an entire sensor array will dramatically increase so that using FDM in a large-scale sensor array is unappealing.

B) General Principles

FIG. 1A shows an exemplary embodiment of the invention. This embodiment is apparatus for magnetic field sensing where the apparatus includes:

1) a magnetic field source 104 configured to provide a modulated magnetic field, where the modulated magnetic field has intervals of zero magnetic field intensity and/or zero crossings of magnetic field intensity;

2) one or more magnetoresistive sensors 102 having electrical resistances that depend on magnetic field intensity at locations of the magnetoresistive sensors, where the magnetoresistive sensors are disposed in the modulated magnetic field; and 3) electrical circuitry 110 configured to provide electrical signals that depend on electrical resistances of the magnetoresistive sensors.

The electrical circuitry is further configured to sample the electrical signals synchronously with the modulated magnetic field. More specifically, the electrical signals are sampled during the intervals of zero magnetic field intensity of the modulated magnetic field and/or at the zero crossings of magnetic field intensity of the modulated magnetic field to provide reference sampled data. The electrical signals are sampled at times the magnetic field intensity of the modulated magnetic field is non-zero to provide measurement sampled data. The apparatus is configured to provide a difference between the measurement sampled data and the reference sampled data as a measurement output.

The net effect of this approach for handling the signals from the MR sensor is to cancel the baseline signal in the measurement output and also to significantly reduce low frequency noise in the measurement output. Here the 'baseline' signal is the signal that is provided by a magnetoresistive sensor in the absence of a magnetic field. Note that magnetoresistance is a change in resistance caused by an applied magnetic field. For example, the resistance may change from R to R+ΔR due to an applied magnetic field, and in this example R is the baseline and ΔR is the magnetoresistive effect. If a current I flows through the sensor, the baseline voltage signal is IR and the magnetoresistive voltage signal is I ΔR. In practice, the total signal (e.g., I(R+ΔR)) is measured and then processed to determine the magnetoresistive part of the total signal. It is convenient to refer to these total signals from magnetoresistive sensors as 'measurement signals' having corresponding 'measurement sampled data', as above.

Practice of the invention does not depend critically on how the difference between the measurement sampled data and the reference sampled data is provided. For example this difference can be provided by an analog difference circuit or by a digital difference circuit. Practice of the invention also does not depend critically on how the modulated magnetic field is provided to the MR sensors. However, it is preferred for this field to be provided in a way that is suitable for integration with MR sensor arrays. For example, the modulated magnetic field can be provided by field wires or integrated circuit traces disposed beneath the array of MR sensor elements.

The magnetic field modulation is preferably periodic. Suitable magnetic field modulation wave forms include, but are not limited to: sinusoids, square waves, and return to zero (RZ) waveforms. Any magnetic field modulation wave form having zero crossings or intervals of zero intensity can be employed. Here a square wave (e.g., 1) of FIG. 4B is defined as periodic modulation between zero intensity and one other non-zero magnetic field intensity, where the field intensity is held constant except when switching between the two states, and the switching pattern is 0+0+0+0+ (or 0−0−0−0−) etc. A return-to-zero (RZ) modulation (e.g., 3) of FIG. 4B) is defined as periodic modulation between zero intensity and two other non-zero magnetic field intensities. Here the two non-zero magnetic field intensities have equal magnitude and opposite polarity. The field intensity is held constant except when switching between the three states, and the switching pattern is 0+0−0+0− (or 0−0+0−0+) etc.

As described in greater detail below, the relation between sampling rate of the electrical signals and modulation frequency of the magnetic field depends on details of the CDS methods being employed. Common options are the modulation frequency of the modulated magnetic field being 1/2 or 1/4 of the sampling rate of the electrical signals.

In preferred embodiments, the apparatus further includes one or more baseline suppressors configured to reduce the direct current (DC) baseline of the magnetoresistive sensors. This can be helpful for preventing saturation when amplifying weak MR signals.

Temperature compensation is an important consideration when using MR sensors. One known approach to MR sensor temperature compensation relies on using the baseline signal to temperature correct the MR signal. Since CDS removes the baseline signal from the measurement output, special measures are needed to combine CDS and temperature compensation.

In an embodiment, the apparatus further includes bias circuitry 108 on FIG. 1A to apply an electrical bias to the magnetoresistive sensors 102, where the electrical bias is modulated synchronously with the modulated magnetic field between a first bias and a second bias.

The electrical signals are sampled during the intervals of zero magnetic field intensity of the modulated magnetic field and/or at the zero crossings of magnetic field intensity of the modulated magnetic field and when the electrical bias is the first bias to provide first sampled data.

The electrical signals are sampled during the intervals of zero magnetic field intensity of the modulated magnetic field and/or at the zero crossings of magnetic field intensity of the modulated magnetic field and when the electrical bias is the second bias to provide second sampled data.

The apparatus is further configured to provide a difference between the first sampled data and the second sampled data as a baseline output. The measurement sampled data is all sampled at times having the same electrical bias.

The apparatus is further configured to automatically determine a temperature-corrected measurement from the measurement output and the baseline output, and to provide the temperature-corrected measurement as a temperature corrected output.

The first and second sampled data is sampled at two different electrical bias values and at zero magnetic field in order to provide a baseline signal for temperature correction. Details of this are given in section D below.

The magnetoresistive sensors can be configured to be disposed in a magnetic field to be quantified that is superposed with the modulated magnetic field. For example, the magnetic field to be quantified can be generated by magnetic particles 106 on FIG. 1A captured on or near surfaces of the magnetoresistive sensors. Suitable magnetic particles include but are not limited to: superparamagnetic particles, antiferromagnetic particles, and ferromagnetic particles with near-zero remanence. The magnetic particles can be conjugated to analytes of interest, and the apparatus can be configured to quantify the analytes (e.g., in a biological assay).

Figure 10:
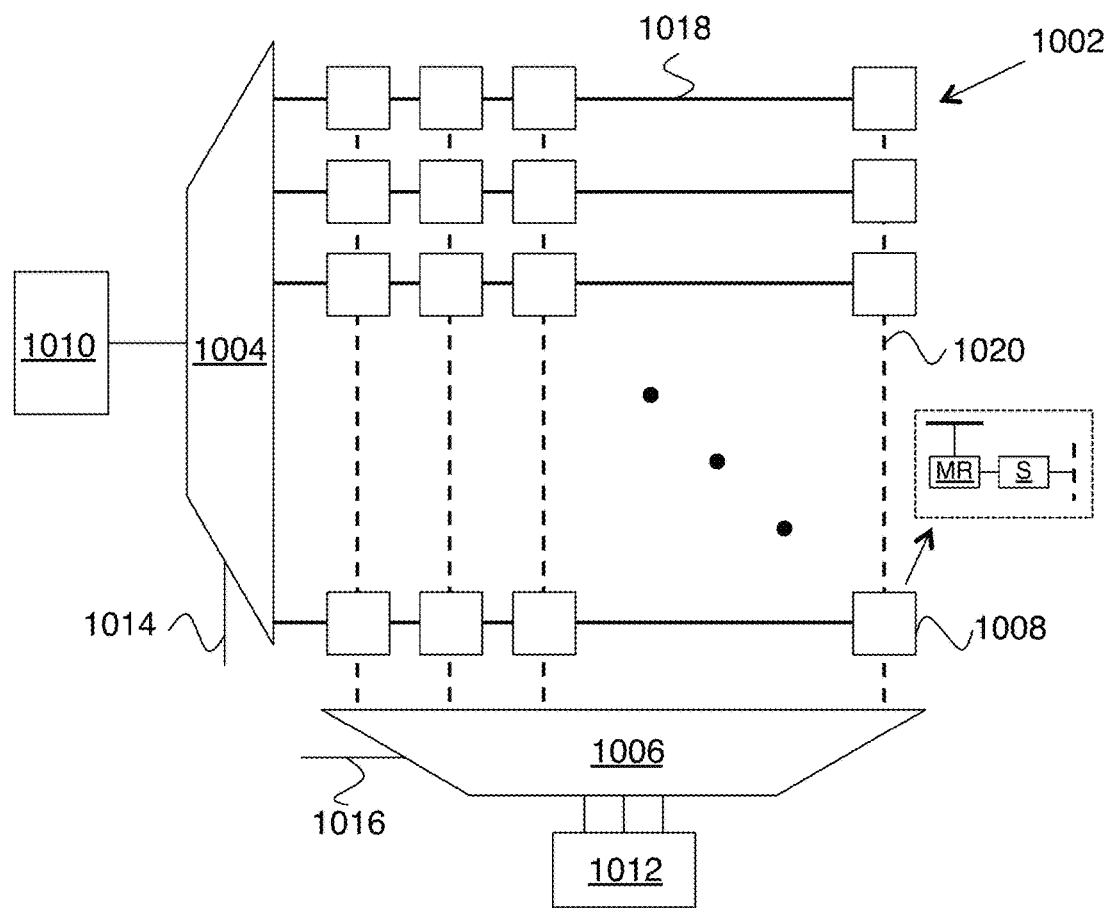
FIG. 10 shows a low noise architecture for an MR sensor array.

The second aspect of this work relates to low noise MR sensor array architectures. An exemplary embodiment is apparatus for magnetic field sensing, where the apparatus includes:

1) a 2-D array of magnetoresistive sensors (1002 on FIG. 10);

2) an analog demultiplexer (1004 on FIG. 10) for selectively providing excitation to one of the rows or columns of the 2-D array; and 3) an analog multiplexer (1006 on FIG. 10) for selectively reading signals out from one of the rows or columns of the 2-D array.

The demultiplexer and multiplexer function as row and column selectors respectively, or vice versa. Each magnetoresistive sensor (MR on FIG. 10) of the 2-D array has an associated sensor switch (S on FIG. 10). The sensor switches are configured to disable all sensors being read out by the multiplexer except the sensor being driven by the demultiplexer (e.g., FIG. 11).

C) Correlated Double Sampling (CDS)

Figure 4A:
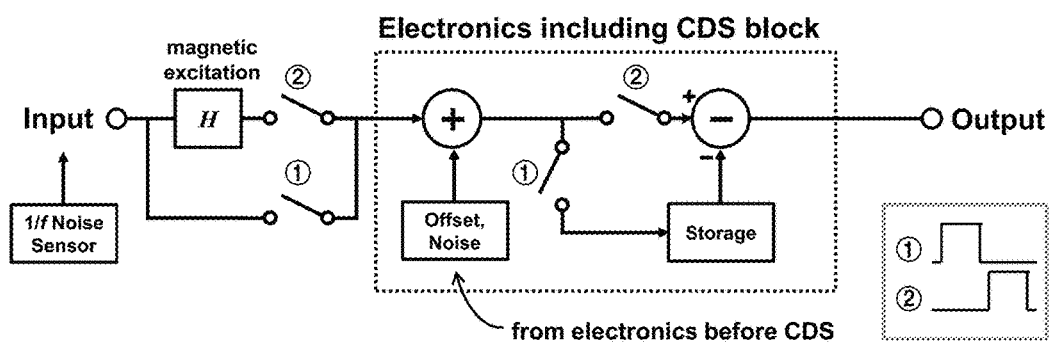
FIGS. 4A-B show the operation principle of correlated double sampling for magnetoresistive sensors.
Figure 4B:
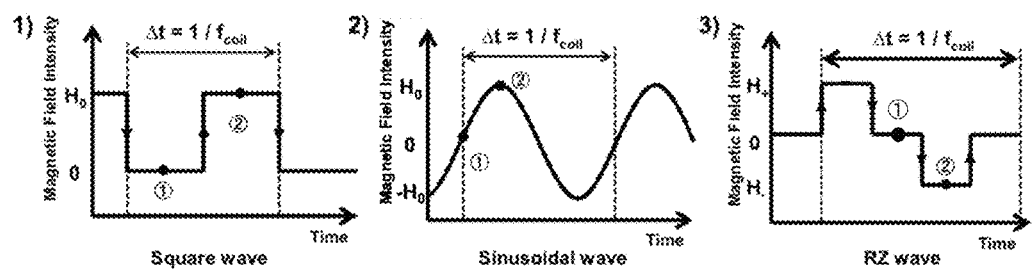

FIGS. 4A-B show operation principle of correlated double sampling for magnetoresistive sensors. FIG. 4A is a conceptual diagram. On/Off timing for electrical switches are shown on the right box as ① and ②. They are non-overlapping. Note that switches inside the dotted box are physical switches in the electrical circuitry, while the switches to the right of the magnetic excitation block are not physical elements. Instead, they schematically represent the modulation of the magnetic field. FIG. 4B shows examples of suitable magnetic field modulation wave forms: 1) square, 2) sinusoidal and 3) return-to-zero (RZ). ①when H field=0 and ② when H field in non-zero.

In general terms, CDS is a known circuit design technique in order to eliminate background noise such as non-ideal offsets and 1/f noise from measured signals of interest. The basic idea is to first sample and store background noise only in the form of electronic charges by capacitors. Then signal+ background is sampled and stored again right after the former capturing event. A difference circuit subtracts one from the other, and thereby only the signal of interest remains. The order of sampling events can be swapped. There are many examples of utilization of the CDS technique. A common application is the integrated image sensors widely used in cameras. Another research group has proposed the CDS technique in connection with a capacitive position sensing system.

In this work we provide a novel CDS technique to effectively suppress the background noise and offsets of the magnetoresistive sensors (FIG. 4A). It utilizes a modulated magnetic field as a signal excitation source. A modulated magnetic field of square, sinusoidal or return-to-zero waveforms are applicable to our CDS techniques (FIG. 4B). Other types of waveform which passes zero magnetic field point can also be utilized. A conventional MR sensor and the sandwich assay technique can be utilized as a sensor and its biological interface. Since MR sensors respond to the in-plane magnetic fields on their magnetic free layers, the presence of the modulated field changes the magnetoresistance of the sensors. If there is zero magnetic field, a sensor under test produces only baseline signal and noise. On the other hand, it will produce finite magnetoresistive signal as well as baseline signal and noises in the presence of non-zero magnetic field. Provided that temporal difference between two measurements (① and ②) is sufficiently small, the 1/f noise and offset from sensors and electronics at ① and ② become highly correlated and thereby the subtraction between two measured data will remove a large portion of 1/f noise and offset. Therefore a signal having reduced 1/f noise and reduced offset can be obtained using the present CDS technique.

D) Correlated Double Sampling with Temperature Correction

Because the MR sensor has both resistive and magnetoresistive properties, it has not only the temperature coefficient of resistance (TCR) but also the temperature coefficient of magnetoresistance (TCMR). Because the MR signal obtained by the present CDS technique is a complex function of TCR and TCMR and it is sensitive to the temperature change, a special temperature correction treatment is required. In this work, we show how to provide temperature correction for the CDS MR sensor technique.

Figure 5:
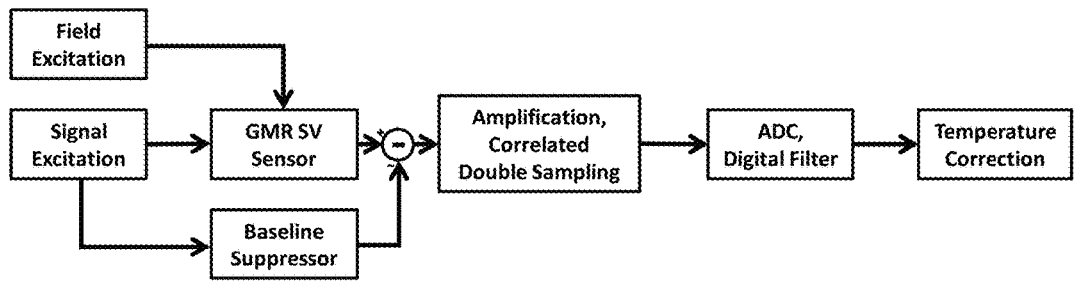
FIG. 5 shows an overall functional diagram for the data acquisition system with correlated double sampling and temperature compensation techniques.

FIG. 5 shows the overall functional diagram for the data acquisition system with CDS and TC techniques. This signal path is utilized for the measurement of both the CDS signal and the baseline signal.

In order to minimize the temperature fluctuation effect on the sensor in CDS, the system with a proper temperature correction (TC) technique is provided (e.g., FIG. 5). In order to increase the gain of the signal path without saturation, the baseline suppressor is introduced. The suppressor can be any circuit having the effect of reducing the baseline from the MR sensors. For example, the suppressor can be a current source, current-mode digital to analog converter, or a R-2R ladder to increase the tolerance against the process variation of the MR sensor. The output of the baseline suppressor subtracted from the output of MR sensor under no magnetic field is the net baseline signal comparable to the magnitude of the MR signal. The suppressed baseline and MR signal are amplified and provided to the correlated double sampler. The processed signal can be digitized and filtered in the digital domain. Finally, a novel temperature correction algorithm eliminates temperature drift noise from the measured data which can be realized in the software domain.

The baseline signal is used to extract the degree of the temperature drift at the moment, and the extracted information of temperature drift is utilized to compensate the measured MR signal to make it temperature insensitive. Because the CDS operation for obtaining MR signal ($V_{MR}$) also removes the baseline signal from measured signal, a unique method to measure only the baseline signal ($V_{BASE}$) is necessary. In order to improve the performance of the temperature correction, $V_{BASE}$ should be 1/f noise and offset-reduced. It employs an additional CDS phase during the operation.

Figure 6A:
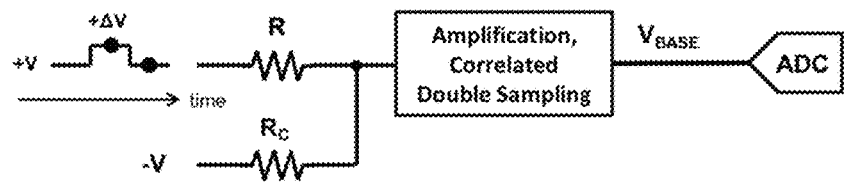
FIG. 6A shows CDS for acquisition of the baseline signal.
Figure 6B:
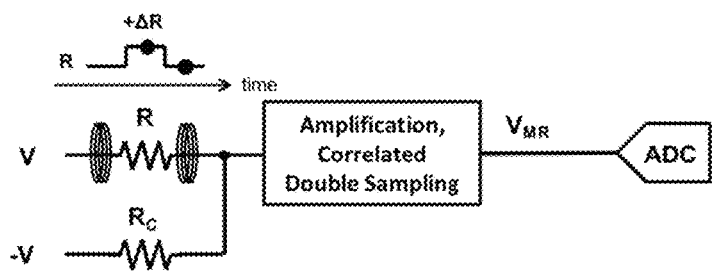
FIG. 6B shows CDS for acquisition of the MR signal.

FIG. 6A shows correlated double sampling technique for 1/f noise and offset-reduced baseline signal. FIG. 6B shows correlated double sampling technique for 1/f noise and offset-reduced MR signal detection. In FIG. 6A, the electrical bias voltage into the MR sensor is given pulsed form. In FIG. 6B, the pulsed external magnetic field (schematically shown by two coil symbols around R) is provided to the sensor, thereby changing the resistance of the MR sensor. R and Rc are the MR sensor and the baseline suppressing resistor, respectively. Dots on the timing graph indicate the moments to be sampled at the correlated double sampler.

Here we provide the novel correlated double sampling techniques to measure both the 1/f noise and offset-reduced baseline signal and the MR signal (FIGS. 6A-B). The virtues of this approach include: 1) the simplicity in the circuit design because the correlated double sampling in FIGS. 6A-B shares most of the signal path; and 2) the magnetic field modulation is utilized in the correlated double sampling. To measure the 1/f noise and offset-reduced baseline signal, the bias voltage exciting the MR sensor R gets a pulsed form. It changes from V to V+ΔV and going back to V (FIG. 6A). CDS operation is done by sampling the baseline signal with respect to these two levels. The path output $V_{BASE}$ is $$V_{BASE} = \left(\left(\frac{V+\Delta V}{R} + \frac{-V}{R_C}\right) - \left(\frac{V}{R} + \frac{-V}{R_C}\right)\right)G_{PATH} = \frac{\Delta V}{R}G_{PATH}$$

$$R = \frac{\Delta V}{V_{BASE}}G_{PATH}$$

where $G_{PATH}$ is the transimpedance gain of the analog circuits. Since $V_{BASE}$ results from the CDS operation, it is 1/f noise and offset-reduced. So is R.

For measuring the MR signal, the pulsed external magnetic field from 0 to ΔH is applied to the MR sensor (FIG. 6B). Its resistance corresponding to the field changes from R to R+ΔR. The MR signal in voltage, $V_{MR}$, is $$V_{MR} = \left(\left(\frac{V}{R+\Delta R} + \frac{-V}{R_C}\right) - \left(\frac{V}{R} + \frac{-V}{R_C}\right)\right)G_{PATH} \approx -\frac{\Delta R}{R^2}G_{PATH}V$$

$$\frac{\Delta R}{R^2} \approx -\frac{V_{MR}}{G_{PATH}V}$$

Like the former case, $$\frac{\Delta R}{R^2}$$

is 1/f noise and offset-reduced.

Because the sensors are resistive, the expression of the measured output voltage depends on the type of excitation methods: voltage and current excitation. A common voltage excitation method generates the output voltage containing the reciprocal terms of the resistance of sensors. On the other hand, a common current excitation method produces the output voltage including the proportional terms of the resistance of sensors. An example derivation for the output signal of the current excitation method is shown here.

$$V_{out} = I \cdot R = IR_0(1 + \alpha T)$$

where I and $\alpha$ is the excitation current and the temperature coefficient of resistance, respectively.

We provide here a new temperature correction algorithm suitable for use in connection with CDS MR sensors.

We define the following terms.

$G_{PATH}$: temperature insensitive transimpedance gain of the analog circuits $R_0$, $\Delta R_0$: temperature independent resistance and magnetoresistance, respectively $\alpha$, $\beta$: temperature coefficient of nominal resistance and magnetoresistance, respectively $V_{MR,measured}(t)$: the measured MR signal (temperature sensitive)

$V_{BASE,measured}(t)$: the measured baseline signal (temperature sensitive)

$V_{MR,corrected}(t)$: the desired MR signal after temperature correction $\Delta T$: temperature change at time t comparing to the initial temperature at time 0

In the ideal condition where temperature does not change, $V_{MR}$ and $V_{BASE}$ are as follows:

$$V_{MR,Ideal}(t) = G_{PATH} V \left( \frac{1}{R_0 + \Delta R_0} - \frac{1}{R_0} \right) \approx -\frac{G_{PATH} V \Delta R_0}{R_0^2}$$

$$V_{BASE,ideal}(t) = \frac{G_{PATH} \Delta V}{R_0}$$

Including temperature fluctuation effect, $V_{MR}$ and $V_{BASE}$ become $$V_{MR,measured}(t) = -\frac{G_{PATH} V \Delta R_0}{R_0^2} \cdot \frac{1 + \beta \Delta T}{(1 + \alpha \Delta T)^2}$$

$$V_{BASE,measured}(t) = \frac{G_{PATH} \Delta V}{R_0(1 + \alpha \Delta T)}$$

Initial values of these two terms at time 0 are as follows.

$$V_{MR,measured}(0) = -\frac{G_{PATH} V \Delta R_0}{R_0^2}$$

$$V_{BASE,measured}(0) = \frac{G_{PATH} \Delta V}{R_0}$$

Normalizing the MR signal and the baseline signal to their initial magnitude at time 0, $$\frac{V_{MR,measured}(t)}{V_{MR,measured}(0)} = \frac{1 + \beta \Delta T}{(1 + \alpha \Delta T)^2}$$

$$\frac{V_{BASE,measured}(t)}{V_{Base,measured}(0)} = \frac{1}{1 + \alpha \Delta T}$$

First, the temperature dependent component of the nominal resistance in a MR sensor is derived.

$$\alpha \Delta T = \frac{V_{BASE,measured}(0)}{V_{Base,measured}(t)} - 1$$

Next, the temperature dependent component of the magnetoresistance is expressed as follows.

$$\beta \Delta T = \frac{V_{MR,measured}(t)}{V_{MR,measured}(0)} \cdot (1 + \alpha \Delta T)^2 - 1 = $$

$$\frac{V_{MR,measured}(t)}{V_{MR,measured}(0)} \cdot \left( \frac{V_{BASE,measured}(0)}{V_{BASE,measured}(t)} \right)^2 - 1$$

The ratio of the temperature coefficient of MR to that of nominal R is defined here.

$$\kappa \triangleq \frac{\beta}{\alpha} = \frac{\frac{V_{MR,measured}(t)}{V_{MR,measured}(0)} \cdot \left( \frac{V_{BASE,measured}(0)}{V_{BASE,measured}(t)} \right)^2 - 1}{\frac{V_{BASE,measured}(0)}{V_{BASE,measured}(t)} - 1}$$

The equation of $V_{MR,measured}$ can be represented without two temperature coefficients.

$$V_{MR,measured}(t) = -\frac{G_{PATH} V \Delta R_0}{R_0^2} \cdot \frac{1 + \kappa \left( \frac{V_{BASE,measured}(0)}{V_{BASE,measured}(t)} - 1 \right)}{\left( \frac{V_{BASE,measured}(0)}{V_{BASE,measured}(t)} \right)^2}$$

In order to desensitize it from temperature fluctuation, we can multiply it with the term below.

$$V_{MR,corrected}(t) = $$

$$V_{MR,measured}(t) \cdot \frac{\left( \frac{V_{BASE,measured}(0)}{V_{BASE,measured}(t)} \right)^2}{1 + \kappa \left( \frac{V_{BASE,measured}(0)}{V_{BASE,measured}(t)} - 1 \right)} = -\frac{G_{PATH} V \Delta R_0}{R_0^2}$$

So the temperature insensitive magnetoresistive voltage output is derived only with the $V_{MR,measured}$ and $V_{BASE,measured}$, without the knowledge of the temperature coefficients of both nominal resistance and magnetoresistance of the MR sensor.

The algorithm for the temperature correction in case of current excitation on MR sensors is also given here.

$$V_{MR,ideal}(t) = A_{PATH} I((R_0 + \Delta R_0) - R_0) = A_{PATH} I \Delta R_0$$

Considering temperature fluctuation, $$V_{MR,measured}(t) =$$

$$A_{PATH} I \Delta R_0 (1 + \beta \Delta T) = A_{PATH} I \Delta R_0 \left(1 + \kappa \left(\frac{V_{BASE,measured}(t)}{V_{BASE,measured}(0)} - 1\right)\right)$$

where $$\kappa \triangleq \frac{\beta}{\alpha} = \frac{\frac{V_{MR,measured}(t)}{V_{MR,measured}(0)} - 1}{\frac{V_{BASE,measured}(t)}{V_{BASE,measured}(0)} - 1}$$

$A_{PATH}$: temperature insensitive voltage gain of the analog circuits

Temperature desensitization is done by this multiplication.

$$V_{MR,corrected}(t) = V_{MR,measured}(t) \cdot \frac{1}{1 + \kappa\left(\frac{V_{BASE,measured}(t)}{V_{BASE,measured}(0)} - 1\right)} = A_{PATH} I \Delta R_0$$

E) Experimental Work

Figure 7A:
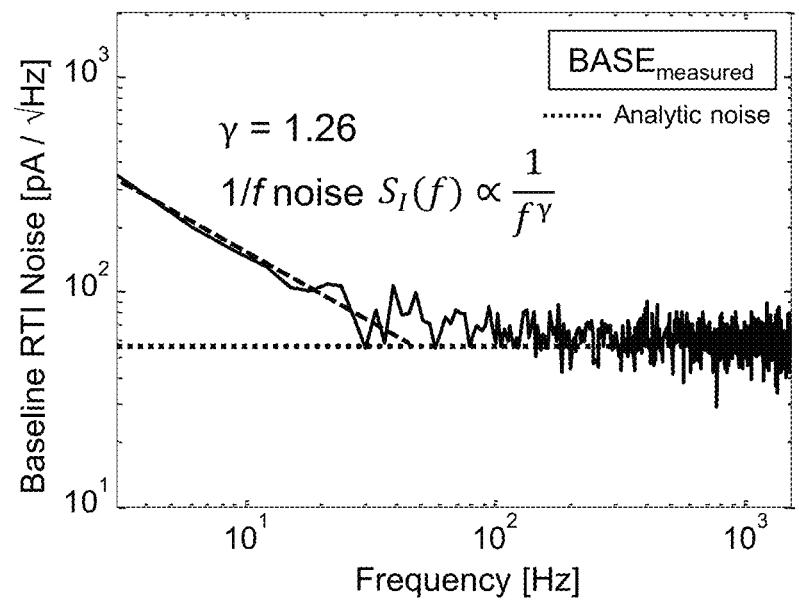
FIGS. 7A-D show experimental results of correlated double sampling for MR sensors.
Figure 7B:
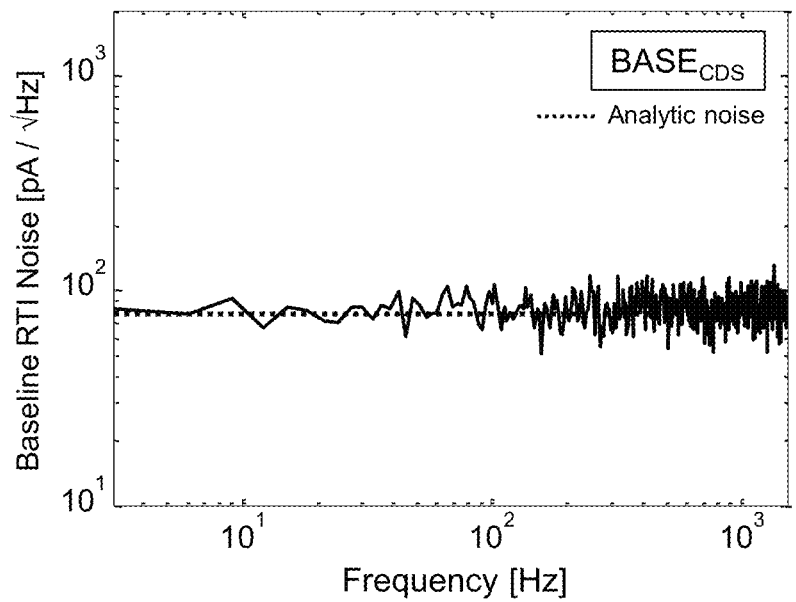
Figure 7C:
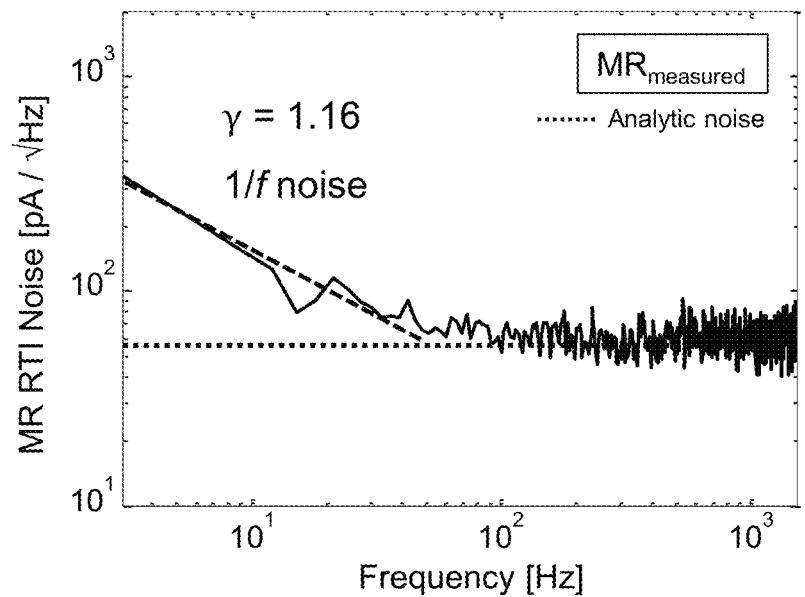
Figure 7D:
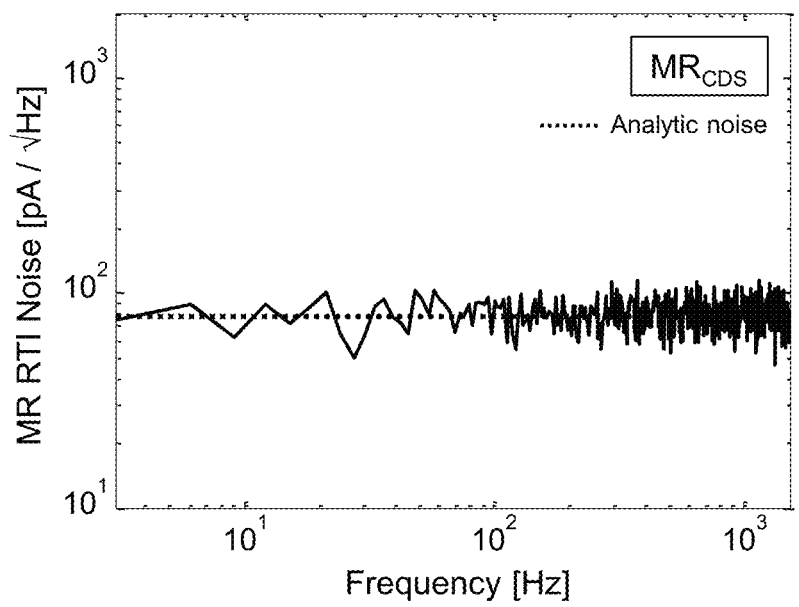

FIGS. 7A-D show experimental results of correlated double sampling. FIG. 7A shows measured referred to input noise (RTI) in baseline. γ is the slope of the 1/f noise. Typically 0.5≤γ≤2. FIG. 7B shows the CDS effect on the results of FIG. 7A. The 1/f noise is eliminated. FIG. 7C shows measured referred to input noise (RTI) in the magnetoresistive signal. FIG. 7D shows the CDS effect on the results of FIG. 7C. Most of the 1/f noise is suppressed.

Figure 8A:
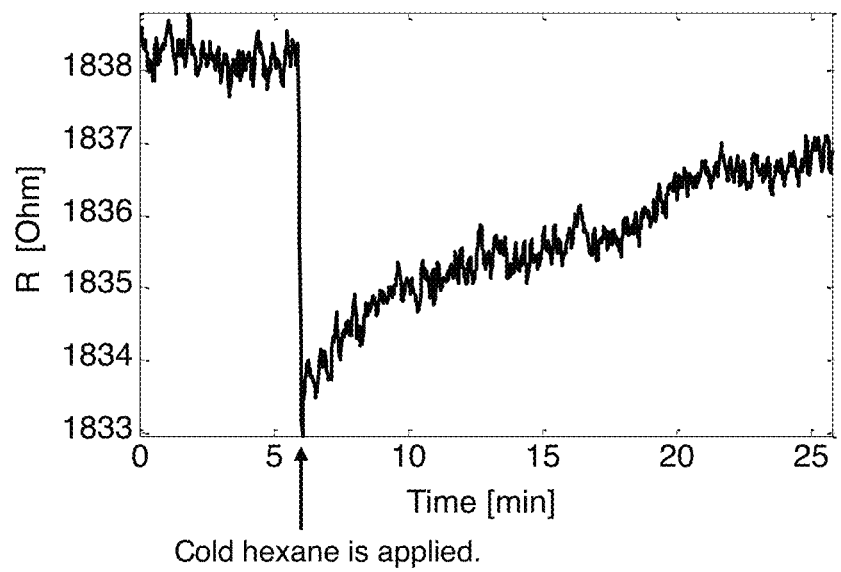
FIGS. 8A-D show experimental results of correlated double sampling combined with temperature compensation for MR sensors.
Figure 8B:
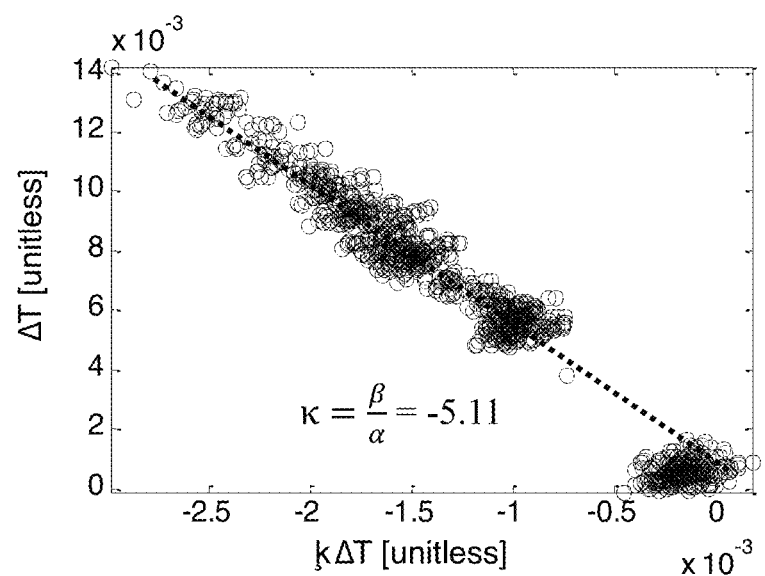
Figure 8C:
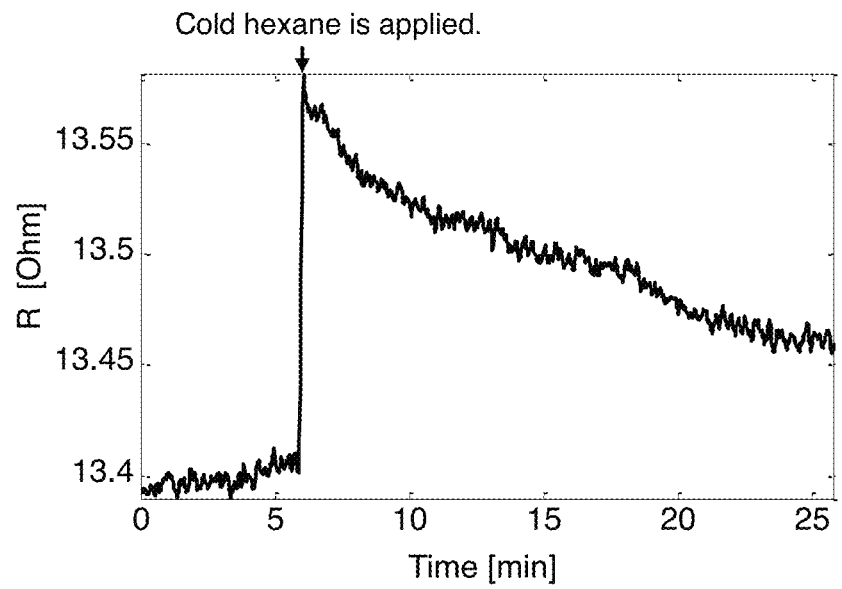
Figure 8D:
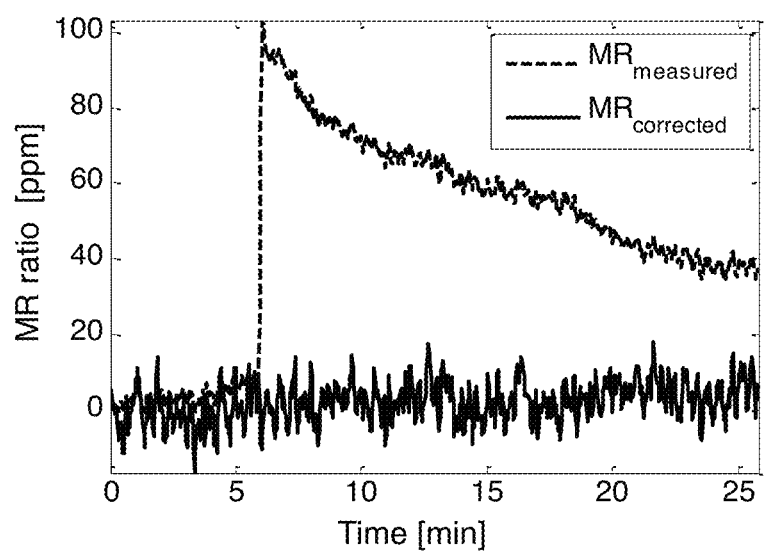

FIGS. 8A-D show experimental results demonstrating temperature correction technique. FIG. 8A shows the response of nominal resistance to the temperature change due to the cold hexane solution applied at six minutes. FIG. 8B shows the response of magnetic resistance. κ (the ratio of TCMR to TCR) is −5.11 and it will be used in the temperature correction of ΔR. FIG. 8C shows the response of magnetic resistance. R and ΔR are simultaneously measured using CDS. FIG. 8D shows the measured AMR ratio (dash curve) and the corrected AMR ratio (solid curve) using the present temperature correction in ppm. The corrected AMR ratio stays at around the 0 ppm regardless of the temperature change.

Figure 9A:
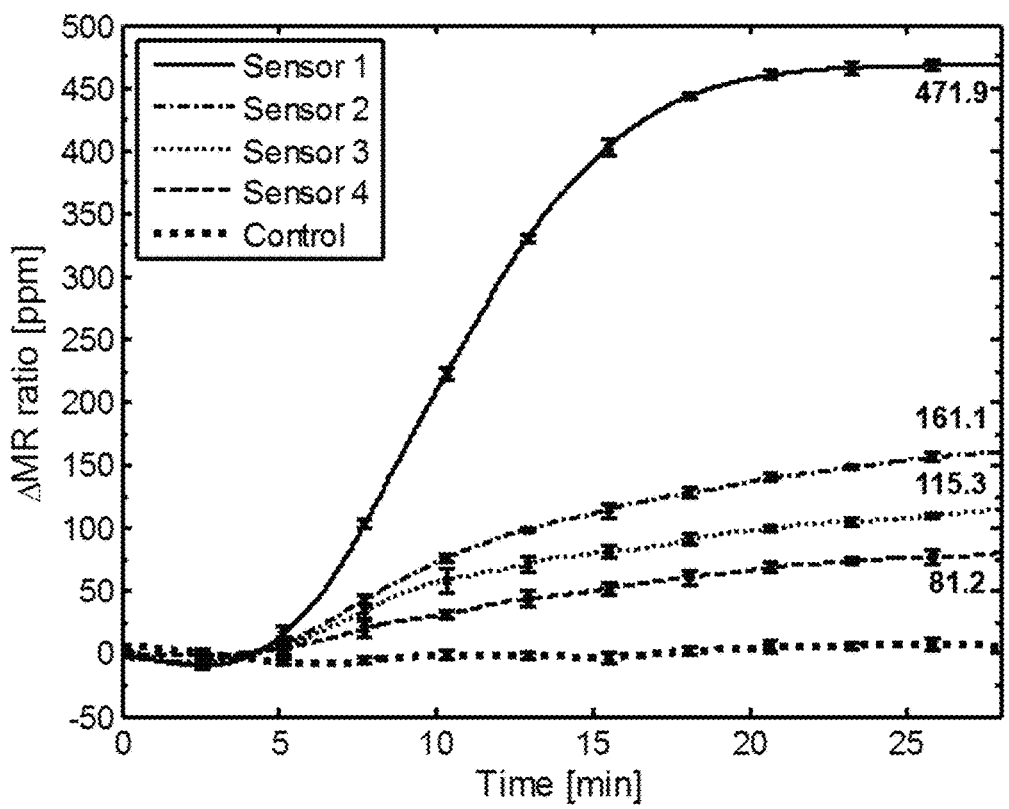
FIG. 9A-E show results from a binding experiment using magnetic nanoparticles.

FIG. 9A shows results from a binding experiment using magnetic nanoparticles. This plot shows binding curves for five sensors, one of which is covered by the thick passivation layer and serves as a control. The control cannot be influenced by nanoparticles on the thick passivation layer because the distance between particles and the control is beyond the limit of the proximity effect of the particles. The error bar represents the noise from binding kinetics and measurement setup.

Figure 9B:
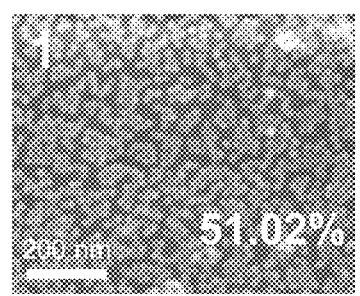
Figure 9C:
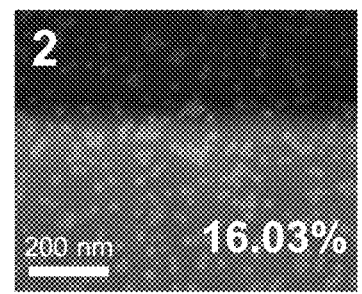
Figure 9D:
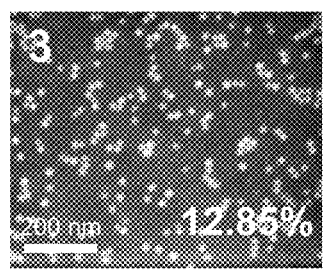
Figure 9E:
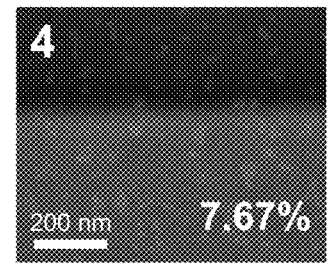

FIG. 9B is an SEM image of sensor 1. Particle coverage is 51.02%. FIG. 9C is an SEM image of sensor 2. Particle coverage is 16.03%. FIG. 9D is an SEM image of sensor 3. Particle coverage is 12.85%. FIG. 9E is an SEM image of sensor 4. Particle coverage is 7.67%.

Experiments to confirm the functionality of the present CDS and TC techniques have been conducted using GMR SV sensors arrays (FIGS. 7A-D and 8A-D). If CDS is not performed in the acquisition of VBASE,measured and VMR,measured, these signals will be contaminated with explicit 1/f noise (FIGS. 7A and 7C). The amplitude of the 1/f noise overwhelms the effect of temperature change on the sensors, thereby temperature correction will not properly work. Utilizing the present CDS technique in the measurement can effectively suppress 1/f noise from the measured signals (FIGS. 7B and 7D). The evaluation result of the present TC is shown in FIGS. 8A-D. When the cold hexane solution is applied to the sensor surface at six minutes, the nominal resistance (R0) and MR rapidly changes corresponding to the abrupt temperature change (FIGS. 8A and 8C). As time goes on, surface temperature starts to return to the original temperature and R0 and MR are restored to the initial values. The ratio of two temperature coefficients is constant regardless of the temperature change (FIG. 8B). With the information of temperature drift extracted from the R0 change, the measured MR can be made temperature-insensitive using the present TC technique (FIG. 8D).

FIGS. 9A-E show results from a binding experiment with $Fe_3O_4$ superparamagnetic nanoparticles of 15 nm in diameter using chemical absorption between Polyethylenimine and the surfactant of the particles. The reaction can be quantitatively measured. Validation of the quantitative result in FIG. 9A has been done analyzing SEM images through the percentage of the area coverage by nanoparticles (FIGS. 9B-E). Therefore it is demonstrated through the experiments that the combination of the present CDS and temperature correction techniques is effective to produce a noise resilient output from magnetoresistive sensors.

To better appreciate this work, we briefly compare these results to earlier double modulation work. This earlier work utilizes double modulation and the Fast Fourier Transform (FFT) to separate the analyte-related signals from background noise and harmonics. In spite of its high frequency resolution and superior thermal noise profile by frequency binning, FFT requires a large number of samples taken for 500 milliseconds to provide a frequency resolution of 2 Hz. It has an additional timing penalty to complete post-processing using measured samples, which is comparable to or more than sampling time, e.g., in the order of seconds. These considerations lead to a conclusion that the spectral analysis is not favorable to the large-scale magnetoresistive (MR) sensor array system regardless of in-pixel switching. In order to enhance the readout performance, we need to explore a different readout scheme other than spectral analysis.

Generally, a large-scale sensor array contains a thousand or more sensors. In order to guarantee real time analysis using a magnetoresistive biosensor array, the system needs to measure the entire array within a specified period of time. Despite the conventional spectral analysis having good SNR performance, a long readout time per column (or channel) can be a fatal disadvantage for real time analysis in bioassays. So fast readout performance is crucial to large-scale MR sensor arrays and corresponding measurement systems.

Correlated double sampling (CDS) as described above can help solve this problem. Basically this technique has been developed in order to mitigate 1/f noise, which is a significant source of noise harming the readout performance of circuits. Theoretically CDS operation just needs two subsequent data acquisitions. If the temporal difference between two acquisitions Δt is getting smaller, CDS can produce 1/f noise-reduced output signals at high speed. This exactly meets our needs to build a high speed data acquisition circuits for large-scale MR sensor arrays. In order to lower the thermal noise, multiple samples of CDS measurements can be taken then averaged. The above described experiments for the proof-of-concept demonstrate that the readout throughput of 48.8 samples per second per channel was achieved when the magnetic field was modulated at 3.125 kHz (2 CDS samples were taken during each period of the field modulation, so the CDS sampling rate was 6.25 KHz) and the 64 CDS output samples are averaged in experiments. These results are 24.4 times faster than the throughput of the conventional double modulation technique with assumptions that the FFT processing penalty is neglected and frequency division multiplexing is not utilized. Therefore, the readout time according to this work is shown to be faster than the conventional spectral analysis and is favorable to the large-scale MR sensor array and system.

F) Low Noise MR Sensor Array Architecture

Conventional MR sensors arrays consist of only MR sensors and wires in a two dimensional matrix structure like Random Access Memories. They have been scaled up by simply increasing the number of rows and columns. Sensor arrays of this kind having up to 256 elements have been demonstrated.

There is a need for a large-scale microarray to accommodate numerous analyte types of interest among the more than hundreds of thousands of analytes such as human proteins in some biological applications. The conventional way to increase only the number of sensors and wires to more than 256 is hardly achievable because it scales poorly. Connectivity is poor (more pads are required), noise is worse and channel bandwidth is undesirably narrowed.

We provide a MR sensor array architecture which can accommodate more than 10,000 sensors per array. FIG. 10 shows an example. Here 1002 is an MR sensor array. The number of rows and columns can be larger than 100 and thereby more than 10,000 MR sensors can be in the array. The number of pins (or pads) is minimized by utilizing an analog multiplexer 1006 and demultiplexer 1004. Each pixel (e.g., 1008) includes one switch S and one magnetoresistive sensor MR. However, there can be variations for the number of switches inside the pixel. An excitation source 1010 can drive either voltage or current to the sensor array, while multiplexer 1006 provides signals to readout circuitry 1012.

One of the key features of this large-scale MR sensor array is that it has a pair of analog multiplexer (Mux) and demultiplexer (deMux) as column line (heavy dashed lines e.g., 1020) and row line (heavy solid lines e.g., 1018) selectors, respectively. In the example of FIG. 10, 1014 is the row selection input to demultiplexer 1004, and 1016 is the column selection input to multiplexer 1006. Introduction of the Mux and the deMux dramatically reduces the number of input/output pads of the microarray chip, which in turn greatly simplifies the interface with sensor readout circuits. Adopting a two dimensional matrix structure makes the large-scale sensor array to be randomly accessible in time and to be power efficient. However, the fabrication of this array can be complex since both CMOS processes for analog Mux/deMux and non-CMOS post fabrication processes for MR sensors are required, which may increase the total fabrication cost. This cost issue can be resolved by adopting advanced semiconductor fabrication techniques for mass production.

Figure 11:
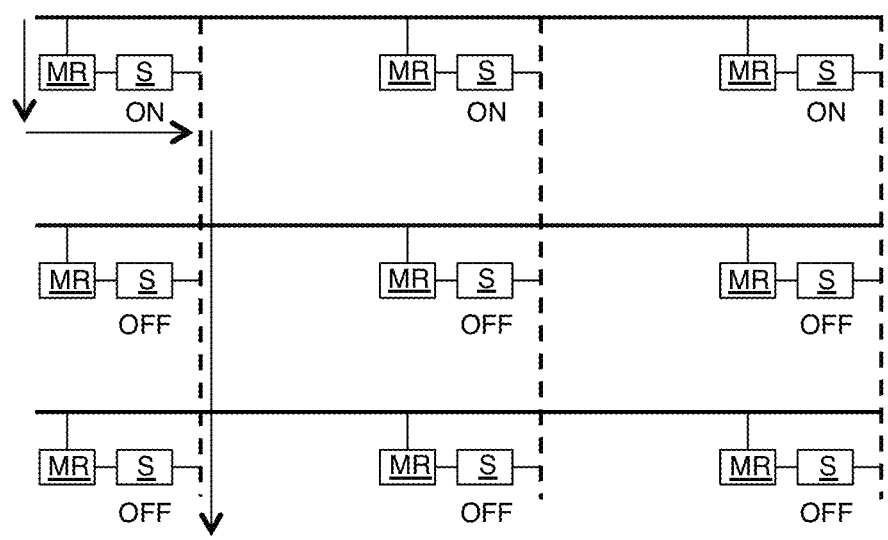
FIG. 11 shows a sensor readout example based on the architecture of FIG. 10.

The other key feature is to introduce a switch S (e.g., a metal-oxide-semiconductor (MOS) device) for each pixel as an on/off switch of a sensor. Only sensors in selected pixels are accessible at specific readout time via a turn-on MOS switch and others are disconnected to the column lines to be read by data acquisition circuits. FIG. 11 shows a sensor readout example. Here the pixel at row 1 and column 1 is measured through a turned-on switch, and the state of all switches is shown by 'ON' or 'OFF' on the figure. Noise generated from other sensors on column 1 is rejected by the turned-off switches. Thus other sensors become transparent when a sensor at row 1 and column 1 is read out by the following readout circuitry on column 1, which improves signal to noise ratio of the data acquisition system. Furthermore, disconnecting unused MR sensors from the column lines also prevents the signal bandwidth of a readout channel from being narrowed.

Figure 12A:
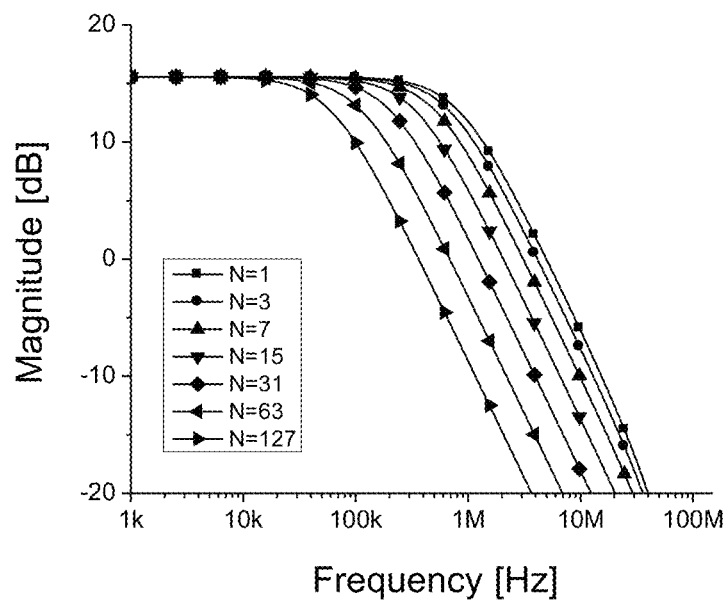
FIGS. 12A-D show AC and noise simulation results relating to the architecture of FIG. 10 (FIG. 12B and FIG. 12D) compared to a conventional MR sensor array (FIG. 12A and FIG. 12C).
Figure 12B:
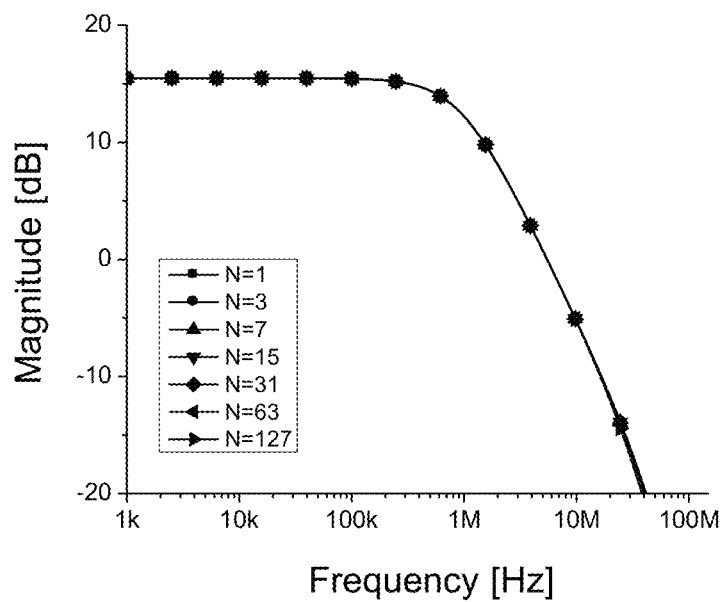
Figure 12C:
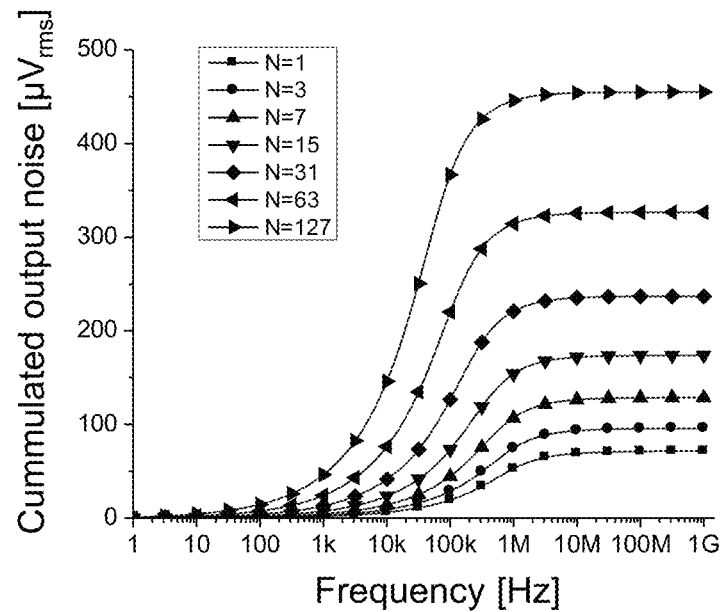

These benefits are demonstrated by an analog circuit simulation as shown on FIGS. 12A-D. These results are from AC simulation and noise simulation results of a transimpedance amplifier which reads an MR sensor out of at most 128 sensors per column. FIGS. 12A and 12C show magnitude and cumulative output noise, respectively, for a conventional MR sensor array (no per-pixel switches). Note that N indicates additional MR sensors attached to the same channel. As N increases, the channel bandwidth gets narrower and the output noise profile gets worse. Both bandwidth and output noise of the amplifier are heavily dependent on the number of sensors per column.

Figure 12D:
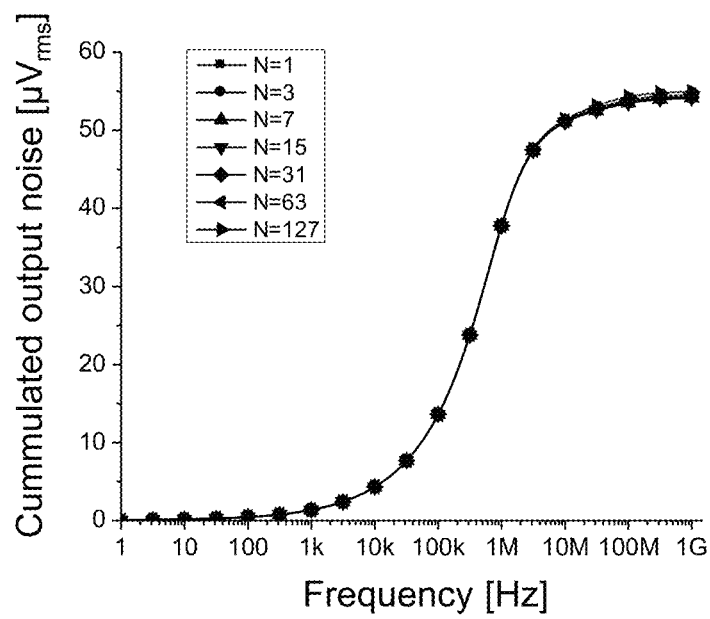

FIGS. 12B and 12D show magnitude and cumulative output noise, respectively, for a sensor array as on FIG. 10 (i.e., including per-pixel switches). Neither bandwidth nor output noise changes as the number of sensors per column increases.

MOS switches for the large-scale MR sensor array are preferred because of their good on/off switching performance. However MOS switches are not required for practicing the invention. For example, switching diodes can also be utilized in a large-scale MR sensor array as signal switches for a simpler implementation.

The invention claimed is:

1. Apparatus for magnetic field sensing, the apparatus comprising:

a magnetic field source configured to provide a modulated magnetic field, wherein the modulated magnetic field has intervals of zero magnetic field intensity and/or zero crossings of magnetic field intensity;

one or more magnetoresistive sensors having electrical resistances that depend on magnetic field intensity at locations of the magnetoresistive sensors, wherein the magnetoresistive sensors are disposed in the modulated magnetic field;

electrical circuitry configured to provide electrical signals that depend on electrical resistances of the magnetoresistive sensors;

wherein the electrical circuitry is further configured to sample the electrical signals synchronously with the modulated magnetic field;

wherein the electrical signals are sampled during the intervals of zero magnetic field intensity of the modulated magnetic field and/or at the zero crossings of magnetic field intensity of the modulated magnetic field to provide reference sampled data;

wherein the electrical signals are sampled at times the magnetic field intensity of the modulated magnetic field is non-zero to provide measurement sampled data;

wherein the apparatus is configured to provide a difference between the measurement sampled data and the reference sampled data as a correlated double sampling measurement output.

2. The apparatus of claim 1, wherein the difference between the measurement sampled data and the reference sampled data is provided by an analog difference circuit.

3. The apparatus of claim 1, wherein the difference between the measurement sampled data and the reference sampled data is provided by an digital difference circuit.

4. The apparatus of claim 1, wherein the magnetic field modulation is periodic.

5. The apparatus of claim 4, wherein the magnetic field modulation wave form is selected from the group consisting of: sinusoids, square waves, and return to zero (RZ) waveforms.

6. The apparatus of claim 1, further comprising one or more baseline suppressors configured to reduce a direct current (DC) baseline of the magnetoresistive sensors.

7. The apparatus of claim 1, further comprising bias circuitry to apply an electrical bias to the magnetoresistive sensors, wherein the electrical bias is modulated synchronously with the modulated magnetic field between a first bias and a second bias;
wherein the electrical signals are sampled during the intervals of zero magnetic field intensity of the modulated magnetic field and/or at the zero crossings of magnetic field intensity of the modulated magnetic field and when the electrical bias is the first bias to provide first sampled data;
wherein the electrical signals are sampled during the intervals of zero magnetic field intensity of the modulated magnetic field and/or at the zero crossings of magnetic field intensity of the modulated magnetic field and when the electrical bias is the second bias to provide second sampled data;
wherein the apparatus is further configured to provide a difference between the first sampled data and the second sampled data as a baseline output;
wherein the measurement sampled data is all sampled at times having the same electrical bias;
wherein the apparatus is further configured to automatically determine a temperature-corrected measurement from the measurement output and the baseline output, and to provide the temperature-corrected measurement as a temperature corrected output.

8. The apparatus of claim 1, wherein the electrical signals have a sampling rate, and wherein a modulation frequency of the modulated magnetic field is 1/2 or 1/4 of the sampling rate of the electrical signals.

9. The apparatus of claim 1, wherein the magnetoresistive sensors are configured as a 2-D array, and further comprising:
an analog demultiplexer for selectively providing excitation to one of the rows or columns of the 2-D array;
an analog multiplexer for selectively reading signals out from one of the rows or columns of the 2-D array;
wherein the demultiplexer and multiplexer function as row and column selectors respectively, or vice versa;
wherein each magnetoresistive sensor of the 2-D array has an associated sensor switch, and wherein the sensor switches are configured to disable all sensors being read out by the multiplexer except the sensor being driven by the demultiplexer.

10. The apparatus of claim 1, wherein the magnetoresistive sensors are configured to be disposed in a magnetic field to be quantified that is superposed with the modulated magnetic field.

11. The apparatus of claim 10, wherein the magnetic field to be quantified is generated by magnetic particles captured on or near surfaces of the magnetoresistive sensors.

12. The apparatus of claim 11, wherein the magnetic particles are selected from the group consisting of: superparamagnetic particles, antiferromagnetic particles, and ferromagnetic particles with near-zero remanence.

13. The apparatus of claim 11, wherein the magnetic particles are conjugated to analytes of interest, and wherein the apparatus is configured to quantify the analytes.

* * * * *